United States Patent [19]

Langerbeins

[11] Patent Number: 4,781,868

[45] Date of Patent: Nov. 1, 1988

[54] METHOD FOR MAKING UNSATURATED ALIPHATIC CARBOXYLIC ACID ANHYDRIDES

[75] Inventor: Klaus Langerbeins, Langen, Fed. Rep. of Germany

[73] Assignee: Röhm GmbH, Darmstadt, Fed. Rep. of Germany

[21] Appl. No.: 937,195

[22] Filed: Dec. 2, 1986

[30] Foreign Application Priority Data

Dec. 18, 1985 [DE] Fed. Rep. of Germany ....... 3544765

[51] Int. Cl.$^4$ .......................... C07C 51/12; C07C 57/04
[52] U.S. Cl. ..................................... 260/549; 560/204; 260/413; 260/546
[58] Field of Search .......................... 260/549, 413, 546

[56] References Cited

U.S. PATENT DOCUMENTS 2,729,651  1/1956  Reppe et al. ..................... 260/343.5

FOREIGN PATENT DOCUMENTS 0180799  5/1986  European Pat. Off. .
2450965  4/1976  Fed. Rep. of Germany .
2844371  4/1979  Fed. Rep. of Germany .
3332018  3/1985  Fed. Rep. of Germany .
3336691  4/1985  Fed. Rep. of Germany .
1523346  8/1978  United Kingdom .
2007666  5/1979  United Kingdom .

OTHER PUBLICATIONS

Chem. Abstr. 103, 54563z (1985).
Chem. Abstr., 103, 177968t (1985).

*Primary Examiner*—Vivian Garner
*Attorney, Agent, or Firm*—Curtis, Morris & Safford

[57] ABSTRACT

Method for making alpha, beta-unsaturated carboxylic acid anhydrides by carbonylation of esters of acrylic acid or methacrylic acid in the presence of a catalyst system containing at least one noble metal from group VIII of the periodic table, for example rhodium, the reaction being carried out at 70° C. to 350° C. and at pressures from 1 to 500 bar in the presence of a halogen or of a halogen compound, and in particular of iodine or an iodine compound, as a promoter.

12 Claims, No Drawings

METHOD FOR MAKING UNSATURATED ALIPHATIC CARBOXYLIC ACID ANHYDRIDES

The present invention relates to methods for making unsaturated aliphatic carboxylic acid anhydrides by reacting esters of unsaturated aliphatic carboxylic acids with carbon monoxide.

Because of their reactivity, the anhydrides of unsaturated carboxylic acids, and particularly of acrylic acid and methacrylic acid, are important starting compounds for the preparation of interesting monomers which are difficult to obtain by other routes.

THE PRIOR ART

The production of aliphatic saturated carboxylic acid anhydrides by the carbonylation of esters of carboxylic acids by the use of nickel- and halogen-containing catalysts is described in U.S. Pat. No. 2,729,651, for example. German Pat. No. 28 44 371 also describes a process for the production of carboxylic acid anhydrides from aliphatic carboxylic acid esters, including, according to the specification, esters of unsaturated aliphatic carboxylic acids, using nickel catalysts. Because of the presence of a specified amount of a free iodine compound, the carbonylation reaction here can be carried out at the usual temperatures of about 70° C. to 250° C. at substantially lower pressures than in the process of the U.S. patent mentioned, for example at about 50 atmospheres as against about 700 atmospheres. The patents cited do not show carbonylations carried out with esters of unsaturated aliphatic carboxylic acids, and particularly with esters of acrylic acid or methacrylic acid, to give unsaturated carboxylic anhydrides, nor do they give any information on how such carbonylations might be carried out.

Experiments attempting to carbonylate methyl methacrylate in the presence of nickel catalysts and methyl iodide yielded only minor amounts of methacrylic acid nhydride. Rather, considerably larger amounts of the dimerization product of methyl methacrylate were obtained, which product, according to German Pat. No. 33 36 691, is formed by catalytic dimerization in tthe presence of nickel-phosphine complex catalysts.

Carbonylations of acrylic esters carried out by a process described in German Pat. No. 33 32 018 in the presence of alcohols using cobalt carbonyl complexes as catalysts give diesters of succinic acid. Cobalt, along with nickel, is one of the most effective carbonylating metals and, like nickel, is among the iron-triad elements of group VIII of the periodic table.

The carbonylation of a saturated carboxylic acid, namely methyl acetate, in the presence of catalysts containing noble metals of group VIII of the periodic table or compounds thereof, as well as iodine and/or iodine compounds, to give acetic anhydride is described in German Pat. No. 24 50 965.

THE OBJECT OF THE INVENTION

The invention thus has as its object to provide a method for making the valuable unsaturated anhydrides of acrylic and methacrylic acid by the carbonylation of esters of these unsaturated acids.

It has unexpectedly been found that in a catalyzed carbonylation of esters of unsaturated carboxylic acids, the anhydrides of the unsaturated carboxylic acids are formed.

A feature of the invention, therefore, is a method for making unsaturated aliphatic carboxylic anhydrides by reacting an unsaturated aliphatic carboxylic ester with carbon monoxide in the presence of a catalyst which contains a noble metal of Group VIII of the periodic table and/or a compound thereof, optionally with complex ligands, and optionally containing a further cocatalyst, and in the presence of a halogen and/or of a halogen compound, at temperatures from 70° C. to 350° C. and pressures from 1 to 500 bar.

The process of the invention overcomes a prejudice prevailing in the prior art which held that unsaturated esters are carbonylated primarily and solely at the unsaturated carbon atoms so that an introduction of carbon monoxide into the ester group of the unsaturated compounds of carboxylic acid for formation of anhydrides having a double bond does not occur.

ADVANTAGES OF THE INVENTION

With the method of the invention, it now becomes possible to produce corresponding unsaturated carboxylic anhydrides at low cost and in sufficient quantity from such readily available and low cost starting materials as carbon monoxide and many of the known esters of acrylic and methacrylic acid. This has not been feasible by such prior art processes as transanhydridization of unsaturated carboxylic acids with acetic anhydride, for example, or by reacting unsaturated carboxylic acid chlorides with salts of the corresponding acids.

In the carbonylation of an unsaturated carboxylic ester according to the invention, a mixed anhydride is first formed between the unsaturated carboxylic acid component of the ester and the carboxylic acid synthesized from the alcohol component of the starting ester by the introduction of carbon monoxide, which then has a carbon chain that is longer by one carbon atom than that found in the alcohol component of the starting ester.

By reactions which already proceed during the carbonylation reaction, other anhydrides are then formed therefrom, and these will be present in the reaction mixture in amounts depending on the temperature and on the influence of the catalyst. The various anhydrides can be separated from one another as the reaction mixture is worked up, especially by distillation. For example, the carbonylation of methyl methacrylate according to the invention, a mixed anhydride is first formed between methacrylic acid and acetic acid, from which methacrylic acid anhydride and acetic acid anhydride will form in substantial amounts even during the carbonylation process. The acetic acid anhydride, the mixed unsaturated-saturated anhydride, and the methacrylic acid anhydride can then be separated from one another by distillation. The mixed anhydride is also a valuable product and may be used as is, for example in carrying out reactions, or it may be converted practically completely by known methods into the unsaturated anhydride, for example methacrylic acid anhydride, and into the anhydride which ultimately is formed from the alcohol component of the ester and which is also a valuable byproduct.

THE PRACTICE OF THE INVENTION

Suitable starting materials in addition to carbon monoxide, which need not be absolutely pure but may contain inert constituents such as nitrogen, carbon dioxide, or methane even in fairly large amounts, for example up to about 50 percent by volume, and optionally minor amounts of hydrogen, are the esters of alpha, beta-unsaturated carboxylic acids of the formula

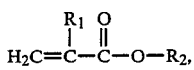

wherein
$R_1$ is H or $CH_3$, and
$R_2$ is alkyl having from 1 to 10 carbon atoms, preferably 1 to 4 carbon atoms, cycloalkyl having from 5 to 10 carbon atoms, alkenyl having from 2 to 10 carbon atoms, aryl, or aralkyl, all of which may contain inert substituents.

Accordingly, suitable esters include the methyl, ethyl, propyl, isobutyl, amyl, decyl, cyclohexyl, allyl, chloroethyl, phenyl, and benzyl esters of acrylic acid and of methacrylic acid. Alkyl esters are preferred and the esters of acrylic and methacrylic acid which are produced on a commercial scale are especially suitable. From an economic viewpoint, it will be preferable to use the $C_1$-$C_4$- alkyl esters, and particularly the methyl esters, in the process of the invention.

In accordance with the invention, the carbonylation of the alpha, beta-unsaturated carboxylic ester to give the unsaturated carboxylic acid anhydride is carried out in the presence of a catalyst which contains as its essential ingredients a noble metal of group VIII of the periodic table and/or a compound thereof, as well as a halogen such as bromine or iodine, or a halogen compound.

The noble metal component of the catalyst may be made up of the elements ruthenium, rhodium, palladium, osmium, iridium, or platinum, either individually or as a mixture of two or more elements. Very active catalysts are obtained when rhodium or rhodium chloride, or palladium or platinum, or compounds thereof, are used in the process of the invention.

The noble metals of group VIII of the periodic table may be used in widely differing forms. For example, the noble metals may be used as such, preferably in the form of finely divided metals of the type known as Raney rhodium or Raney palladium for example, or in the form of simple compounds such as $IrCl_3$, $IrBr_3.3H_2O$, $RuO_2$, $OsO_4$, $PdCl_2$, $Rh(NO_3)_3.2H_2O$, and $Rh_2(SO_4)_3$, or as a noble metal carboxylate such as rhodium(III-)acetate or platinum(II)acetate.

The active catalytic ingredient is preferably a complex compound of the noble metals with a halogen such as chlorine, bromine, and/or iodine; with hydroxyl; water; carbon monoxide; or with suitable compounds of trivalent nitrogen or organophosphine compounds such as tributylphosphine or triphenylphosphine, as complexing agents. The inventive catalysts can also be employed in the form of metal carbonyls or metal carbonyl halides.

The halogen containing component of the catalyst may also vary widely so far as the halogen compound used in it is concerned. Most active are bromine and/or iodine, used particularly in the form of alkyl halides, and preferably of alkyl iodides such as methyl iodide, or as acyl iodides. However, the alkali metal halides, for example, sodium bromide, sodium iodide, potassium bromide, and potassium iodide, or the ammonium salts, as well as the corresponding quaternary ammonium or phosphonium compounds, are also suitable for use as catalyst components.

Promoters which may further be added to the catalyst system and which like the halogen components may be present in a substantial molar excess over the noble metal component are the previously mentioned trivalent nitrogen compounds, for example pyridines, alkylamines, and anilines; trivalent phosphorus compounds such as alkyl phosphines, aryl phosphines, or mixed alkylaryl phosphines; or trivalent arsenic compounds such as triphenylarsenic or analogous compounds of antimony; as well as other known organic complex forming compounds such as lactones, for example, butyrolactone. However, other metals or metal compounds, for example, the carbonyl forming metals Cr, Mo, W, Fe, Co, and Ni, or other metals or metal compounds such as $VCl_3$ and $AlCl_3$, also exhibit good promoter activity.

The catalysts may be used dissolved or in solid form, for example as a finely dispersed suspension. Solid catalysts can also be deposited on commonly used carrier materials such as diatomaceous earth, alumina, or activated carbon and employed also in the form of a fixed bed, for example. The usually liquid unsaturated carboxylic acid esters serve as solvents for the catalysts and as reaction media. When unsaturated carboxylic acid esters are used which are not liquid under the operating conditions, the reaction is carried out in an inert solvent such as carbon tetrachloride, chlorobenzene, hexane, heptane, or cyclohexane.

The ratio of promoter component to active noble metal component in the catalyst system generally ranges from 1:1 to 2000:1, and more particularly from 2:1 to 1000:1, and preferably from 3:1 to 500:1 moles of promoter per atom of noble metal. The amount of the catalyst system, based on the unsaturated carboxylic acid ester used, ranges from 0.01 to 50, and more particularly from 0.05 to 40, and preferably from 0.1 to 25 weight percent.

The reaction is carried out at temperatures ranging from 70° C. to 350° C., and preferably from 100° C. to 250° C. During the reaction, pressures of from 1 to 500 bars, preferably from 1 to 250 bars, and still more preferably from 10 to 150 bars, can be employed.

After working up, for example by filtration and/or distillation, the resulting residue, which contains, among other substances, the noble metal practically quantitatively, can be recycled to a new reaction together with unreacted starting ester and recovered promoters such as methyl iodide.

The novel production process can be practiced both continuously or batchwise. When carried out on a commercial scale, the reaction is preferably performed continuously, which can be done either with a dissolved and/or suspended catalyst or with a fixed catalyst bed.

With a view to preventing undesired polymerizations, the carbonylation process of the invention is best carried out in the presence of effective amounts of polymerization inhibitors such as hydroquinone, hydroquinone monomethyl ether, phenothiazine, or copper compounds.

A better understanding of the present invention and of its many advantages will be had by referring to the following Examples, given by way of illustration.

In the Examples, the percentages given are by weight unless otherwise noted.

EXAMPLES

The stabilization of all batches is effected with 100 ppm of copper oleate. Gas chromatographic separation was effected in a glass capillary column.

EXAMPLE 1

A mixture of 547 mmols of methyl methacrylate, 1 mmol of rhodium(III)chloride ($RhCl_3.3.5H_2O$), 50.8 mmols of triphenylphosphine complexing agent, and 100 mmols of methyl iodide is charged to a 0.35 liter autoclave with a Hastelloy $C_4$ liner, an electric heating system, and a magnetic stirrer. Carbon monoxide is injected at a cold pressure of 100 bar. The autoclave is heated to 200° C. with stirring and held at that temperature for 30 minutes.

The gas chromatogram of the reaction solution indicates 18.2 percent of methacrylic acid anhydride, 29 percent of acetic/methacrylic mixed anhydride, and 12.4 percent of acetic acid anhydride.

COMPARATIVE EXAMPLE

A mixture of 547 mmols of methyl methacrylate, 1.2 mmols of nickel iodide, 50.8 mmols of triphenylphosphine, and 100 mmols of methyl iodide is heated in a 0.35 liter autoclave in a carbon monoxide atmosphere (100 bars cold pressure) at 200° C. for 30 minutes.

The gas chromatogram of the solution indicates 3 percent of 2-methyl-5-methylene adipic acid dimethyl ester, 0.4 percent of methacrylic anhydride, and 1.5 percent of acetic/methacrylic mixed anhydride.

EXAMPLE 2

547 mmols of methyl acrylate, 1 mmol of rhodium-(III)chloride, 50.8 mmols of triphenylphosphine, and 100 mmols of methyl iodide are heated under carbon monoxide (100 bars cold pressure) at 200° C. for 30 minutes.

Gas chromatographic analysis of the solution indicates 26.2 percent of acrylic anhydride, 42.5 percent of acetic/acrylic mixed anhydride, and 24 percent of acetic anhydride.

EXAMPLE 3

547 mmols of methyl methacrylate, 1 mmol of rhodium(III)chloride, 12.0 mmols of molybdenum hexacarbonyl, 50.8 mmols of triphenylphosphine, and 100 mmols of methyl iodide are heated in carbon monoxide atmosphere (100 bars cold pressure) at 200° C. for 30 minutes.

The gas chromatogram indicates 8.9 percent of methacrylic anhydride, 26.8 percent of acetic/methacrylic mixed anhydride, and 24.1 percent of acetic anhydride.

EXAMPLE 4

A mixture of 547 mmols of methyl methacrylate, 1 mmol of rhodium(III)chloride, 33.4 mmols of butyrolactone, 6.4 mmols of triphenylphosphine, and 66.8 mmols of methyl iodide is heated in a carbon monoxide atmosphere (100 bars cold pressures) at 200° C. for 60 minutes.

The gas chromatogram of the solution indicates 9.3 percent of methacrylic anhydride, 18.2 percent of acetic/methacrylic mixed anhydride, and 9.4 percent of acetic anhydride.

EXAMPLE 5

547.0 mmols of methyl methacrylate, 1.0 mmol of platinum(II)chloride, 50.8 mmols of tributylphosphine, and 100 mmols of methyl iodide are heated for 30 minutes at 200° C. in a CO atmosphere (100 bars cold pressure).

According to gas chromatography, 2.8 percent of methacrylic acid anhydride, 1.8 percent of a mixed anhydride of acetic acid and methacrylic acid, and 1.4 percent of acetic anhydride are present.

EXAMPLE 6

547 mmols of methyl methacrylate, 1.0 mmol of rhodium(III)chloride, 50.8 mmols of tributylphosphine, and 100 mmols of acetyl chloride are heated for 30 minutes at 200° C. in a CO atmosphere (90 bars cold pressure).

A gas chromatograph of the solution shows 2.6 percent of methacrylic acid anhydride, 2.5 percent of a mixed anhydride of acetic acid and methacrylic acid, and 0.7 percent of acetic acid anhydride.

EXAMPLE 7

547 mmols of methyl methacrylate, 1.0 mmol of rhodium(III)chloride, 50.8 mmols of tributylphosphine, and 100 mmols of ethyl iodide are heated for 30 minutes at 200° C. in a CO atmosphere (100 bars cold pressure).

According to gas chromatography, 13.9 percent of methacrylic acid anhydride, 26.6 percent of a mixed anhydride of acetic acid and methacrylic acid, and 20.2 percent of acetic acid anhydride are present.

EXAMPLE 8

547 mmols of ethyl methacrylate, 1.0 mmol of rhodium(III)chloride, 50.8 mmols of tributylphosphine, and 100 mmols of methyl iodide are heated for 1 hour at 200° C. in a CO atmosphere (100 bars cold pressure).

According to gas chromatography, 0.5 percent of methacrylate acid anhydride, 1.3 percent of the mixed anhydride of acetic acid and methacrylic acid, and 0.5 percent of acetic acid anhydride are present.

EXAMPLE 9

547 mmols of methyl methacrylate, 1.0 mmol of rhodium(III)iodide, 50.8 mmols of triphenylphosphine, and 100 mmols of methyl iodide are heated for 30 minutes at 200° C. in a CO atmosphere (100 bars cold pressure).

The gas chromatographic spectrum shows 14.1 percent of methacrylic acid anhydride, 26.4 percent of the mixed anhydride of acetic acid and methacrylic acid, and 15.3 percent of acetic acid anhydride.

EXAMPLE 10

547 mmols of methyl methacrylate, 1.0 mmol of palladium(II) chloride, 50.8 mmols of triphenylphosphine, and 100 mmols of methyl iodide are heated for 30 minutes at 200° C. in a CO atmosphere (100 bars cold pressure).

The gas chromatographic spectrum shows 3.1 percent of methacrylic acid anhydride, 0.85 percent of the mixed anhydride of acetic acid and methacrylic acid, and 2.5 percent of acetic acid anhydride.

EXAMPLE 11

547 mmols of methyl methacrylate, 1.0 mmol of rhodium(III)chloride, 50.8 mmols of pyridin as complexing agent and 100 mmols of methyl iodide are heated for 30 minutes at 200° C. in a CO atmosphere (100 bars cold pressure).

According to gas chromatography, 2.2 percent of methacrylic acid anhydride, 3.5 percent of the mixed anhydride of acetic acid and methacrylic acid, and 1.5 percent of acetic acid anhydride are present in the solution.

EXAMPLE 12

547 mmols of methyl methacrylate, 1.0 mmol of rhodium(III)chloride, 82.0 mmols of lithium iodide, 50.8 mmols of triphenylphosphine, and 100 mmols of methyl iodide are heated for 30 minutes at 200° C. in a CO atmosphere (100 bars cold pressure).

The gas chromatogram of the solution shows 7.7 percent of methacrylic acid anhydride, 20.8 of the mixed anhydride of acetic acid and methacrylic acid, and 5.6 percent of acetic acid anhydride.

EXAMPLE 13

547 mmols of methyl methacrylate, 2.0 mmols of rhodium(III)acetate, 70 mmols of tributylphosphine, and 100 mmols of $I_2$ are heated for 1 hour at 200° C. in a CO atmosphere (100 bars cold pressure).

Gas chromatographic investigation of the reaction mixture shows that it contains 12.5 percent of methacrylic acid anhydride, 10.2 percent of the mixed anhydride of the acetic acid and methacrylic acid, and 3.0 percent of acetic acid anhydride.

EXAMPLE 14

An experiment analogous to that in Example 1 was carried out without the addition of phosphine.

Gas chromatography of the reaction solution shows that it contains 1.0 percent of methacrylic acidanhydride, 2.0 percent of the mixed anhydride of acetic acid and methacrylic acid, and 0.7 percent of acetic acid anhydride.

EXMAPLE 15

547 mmols of methyl methacrylate, 1 mmol of rhodium(III)chloride, 0.5 mmol of platinum(II)chloride, 50.8 mmols of tributylphosphine and 100 mmols of methyl iodide are heated under carbon monoxide (100 bars cold pressure) at 200° C. for 30 minutes.

Gas chromatographic analysis of the solution indicates 13.8 percent of methacrylic acid anhyride, 13.7 percent of the mixed anhydride of acetic acid and methacrylic acid, and 4.4 percent of acetic acid anhyride.

What is claimed is:

1. A method for making an unsaturated aliphatic carboxylic anhydride, which method comprises reacting carbon monoxide, at a temperature from 70° C. to 350° C. and at a pressure from 1 to 500 bars, with an unsaturated carboxylic acid ester of the formula

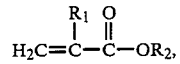

wherein
$R_1$ is H or $CH_3$, and
$R_2$ is alkyl having from 1 to 10 carbon atoms, in the presence of a catalyst system consisting essentially of at least one noble metal from group VIII of the periodic table and a promoter selected from the group consisting of halogens and halogen compounds.

2. A method as in claim 1 wherein said noble metal is selected from the group consisting of rhodium, palladium, and platinum.

3. A method as in claim 1 wherein said promoter is selected from the group consisting of iodine and iodine compounds.

4. A method as in claim 1 wherein $R_2$ is alkyl having from 1 to 4 carbon atoms.

5. A method as in claim 1 wherein said ester is methyl acrylate.

6. A method as in claim 1 wherein said ester is methyl methacrylate.

7. A method for making an unsaturated aliphatic carboxylic anhydride, which method comprises reacting carbon monoxide, at a temperature from 70° C. to 350° C. and at a pressure from 1 to 500 bars, with an unsaturated carboxylic acid ester of the formula

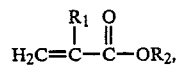

wherein
$R_1$ is H or $CH_3$, and
$R_2$ is alkyl having from 1 to 10 carbon atoms, in the presence of a catalyst system consisting essentially of at least one noble metal from group VIII of th Periodic Table, a promoter selected from the group consisting of halogens and halogen compounds, and a tertiary organic phosphorus compound or a tertiary organic nitrogen compound as a complexing agent.

8. A method as in claim 7 wherein said noble metal is selected from the group consisting of rhodium, palladium, and platinum.

9. A method as in claim 7 wherein said promoter is selected from the group consisting of iodine and iodine compounds.

10. A method as in claim 7 wherein $R_2$ is alkyl having from 1 to 4 atoms.

11. A method as in claim 7 wherein said ester is methyl acrylate.

12. A method as in claim 7 wherein said ester is methyl methacrylate.

* * * * *